United States Patent
Bonrath et al.

(10) Patent No.: US 7,935,849 B2
(45) Date of Patent: May 3, 2011

(54) PROCESS FOR THE PREPARATION OF SATURATED ALIPHATIC KETONES

(75) Inventors: Werner Bonrath, Freiburg (DE); Thomas Kircher, Visp (CH); Rolf Kuenzi, Basel (CH); Johannes Tschumi, Baltschieder (CH)

(73) Assignee: DSM IP Assets B.V., Heerlen (NL)

( * ) Notice: Subject to any disclaimer, the term of this patent is extended or adjusted under 35 U.S.C. 154(b) by 374 days.

(21) Appl. No.: 11/661,376

(22) PCT Filed: Sep. 14, 2005

(86) PCT No.: PCT/EP2005/009510
§ 371 (c)(1), (2), (4) Date: Mar. 29, 2007

(87) PCT Pub. No.: WO2006/029737
PCT Pub. Date: Mar. 23, 2006

(65) Prior Publication Data
US 2008/0139856 A1    Jun. 12, 2008

(30) Foreign Application Priority Data
Sep. 14, 2004 (EP) .................................... 04021775

(51) Int. Cl.
*C07C 45/62* (2006.01)

(52) U.S. Cl. ......... 568/387; 568/388; 568/395; 568/396
(58) Field of Classification Search .................. 568/387, 568/388, 395, 396
See application file for complete search history.

(56) References Cited

U.S. PATENT DOCUMENTS

| | | | | |
|---|---|---|---|---|
| 2,272,122 A | * | 2/1942 | Lee ................................ | 568/396 |
| 6,380,437 B1 | * | 4/2002 | Shi et al. ........................ | 568/405 |
| 2002/0161263 A1 | * | 10/2002 | Shi et al. ........................ | 568/343 |
| 2004/0249218 A1 | * | 12/2004 | Wiese et al. ................... | 568/387 |

FOREIGN PATENT DOCUMENTS

| | | |
|---|---|---|
| EP | 1 106 597 A1 | 11/2000 |
| EP | 1 179 520 A1 | 2/2002 |
| WO | WO 03/031383 A1 | 4/2003 |

OTHER PUBLICATIONS

Taylor, David R., *The Chemistry of Allenes*, University of Manchester Institute of Science and Technology, pp. 317, 334 & 336 (1967).

* cited by examiner

*Primary Examiner* — Sikarl A Witherspoon
(74) *Attorney, Agent, or Firm* — Nixon & Vanderhye P.C.

(57) ABSTRACT

Saturated aliphatic ketones, e.g. hexahydropseudoionone, may be prepared by hydrogenating an olefinically unsaturated ketone, e.g. pseudoionone in a continuous fixed-bed mode in the absence of a solvent in the presence of a catalyst comprising a noble metal deposited on a carrier.

10 Claims, No Drawings

PROCESS FOR THE PREPARATION OF SATURATED ALIPHATIC KETONES

This application is the U.S. national phase of international application PCT/EP2005/009510 filed 14 Sep. 2005 which designated the U.S. and claims benefit of EP 04021775.4, dated 14 Sep. 2004, the entire content of which is hereby incorporated by reference.

The present invention relates to a process for the preparation of saturated aliphatic ketones, especially for the synthesis of 6,10-dimethyl-undecane-2-one (hexahydropseudoionone) from pseudoionone (6,10-dimethyl-undeca-3,5,9-triene-2-one) or from geranylacetone (6,10-dimethyl-undeca-5,9-diene-2-one) and of 6,10,14-trimethylpentadecane-2-one from 6,10,14-trimethyl-pentadeca-4,5-dien-2-one. Saturated aliphatic ketones, e.g., hexahydropseudoionone and 6,10,14-trimethylpentadecane-2-one are known intermediates, e.g. in the preparation of isophytol, a main building block in vitamin E and K syntheses (Ullmann's Encyclopedia of Industrial Chemistry, 5$^{th}$ ed on CD-rom, Vitamins, chapter 4.11).

Pseudoionone can be synthesized from citral, or dehydrolinalool by aldol reaction, Carroll-reaction or Saucy-Marbet-reaction. For details of these $C_3$-elongations see also Ullmann's Encyclopedia of Industrial Chemistry, l.c. Hexahydropseudoionone can be converted into isophytol by a reaction sequence of $C_2$- and $C_3$-elongation followed by hydrogenation, which, in turn can be converted into vitamin E by condensation reaction with 2,3,6-trimethylhydroquinone, see Ullmann's Encyclopedia of Industrial Chemistry Vol A 27 (1996) p. 484. The compound, 6,10,14-trimethylpentadecane-2-one, can be converted into isophytol by ethynylation and Lindlar-type hydrogenation or reaction with a vinyl-Grignard reagent, see WO2004/018400 and WO03/029175.

Known hydrogenation procedures e.g., for the preparation of hexahydropseudoionone by hydrogenation of pseudoionone (e.g. as disclosed in WO2004/007413) suffer from disadvantages such as short lifetime of catalyst, low space-time-yield, need for separation of catalyst, difficult handling of catalyst, and low selectivity.

The present invention provides a novel and efficient process for the preparation for the preparation of saturated aliphatic ketones which process comprises hydrogenating an olefinically unsaturated ketone in a continuous mode in the absence of a solvent in the presence of a catalyst comprising a noble metal deposited on a carrier selected from $TiO_2$, activated C, $ZrO_2$, $SiO_2$ and or $Al_2O_3$ wherein the amount of noble metal is 0.1 to about 5% (wt./wt.), preferably about 0.2 to 0.7% (wt./wt.). The noble metal used in the process of the present invention is preferably palladium while other noble metals conventionally used in hydrogenation processes; e.g. platinum may also find use.

The carrier for the noble metal may be any $TiO_2$, activated C, $ZrO_2$, $SiO_2$ or $Al_2O_3$ carrier conventionally used for fixed-bed hydrogenation processes. Preferred carriers are $SiO_2$, for instance precipitated, silica gel, or pyrogenic silica (sold by degussa under the trade name Aerolyst®), $TiO_2$, for instance precipitated or pyrogenic $TiO_2$ (such as available from DEGUSSA under the trade name Aerolyst®), and $Al_2O_3$, with a pore volume of 0.1-1.5 ml/g, preferred 0.2-1.2 ml/g, and a surface area of 10-400 m$^2$/g, preferred 30-200 m$^2$/g. Preferably, the catalyst, i.e., the carrier loaded with noble metal is distributed within unloaded carrier material in an overall ratio of about 1:1 parts by volume. More preferably, the catalyst is distributed within unloaded carrier material to provide in the reactor an increase of the concentration of noble metal from the entrance to the exit of the flow of the reactants. Thus, for example, the reactor may be charged at the entrance site to one third of its volume with a mixture of one part by volume of catalyst and 2 parts by volume of unloaded carrier material; in the middle part with a mixture of 2 parts by volume of catalyst and 1 part by volume of unloaded carrier material; and at the exit site to one third of its volume with catalyst only. The unloaded carrier material may be the same as the carrier on which the noble metal is deposited, or may by any other carrier material which is inert under the reaction conditions, e.g., inorganic material such as graphite, $TiO_2$, $SiO_2$, $Al_2O_3$, $ZrO_2$.

The hydrogenation in accordance with the invention is suitably carried out under elevated pressure, e.g., at a pressure of about 50 to about 200 bar, especially about 90 to about 160 bar, most preferably at about 120 bar to 155 bar. The reaction temperature is suitably between about 70° C. and about 250° C., preferred about 100° C. and about 220° C., more preferred about 120° C. and 210° C. with the higher temperature prevailing at the entrance site of the reactor. The hydrogenation is suitably carried out using a stoichiometric excess of hydrogen, e.g. using 2-10 times, suitably 4-6 times the theoretically required amount of hydrogen. Further, the hydrogenation is suitably carried out at a mass flow of 1-20, preferably 3-15 [kg of feed per kg of catalyst per hour] (hereinafter: WHSV). The catalyst life-time is higher than 3000 h without loss on activity and selectivity.

The hydrogenation process in accordance with the present invention is of particular interest for the hydrogenation of pseudoionone or of geranylacetone or dihydro geranylacetone to produce hexahydropseudoionone; and for the hydrogenation of 6,10,14-trimethyl-pentadeca-4,5-dien-2-one to produce 6,10,14-trimethyl-pentadecan-2-one. Another example of the hydrogenation of an unsaturated aliphatic ketone in accordance with the present invention is the hydrogenation of dihydrolinalool to form tetrahydrolinalool.

The invention is illustrated further by the Examples, which follow.

EXAMPLE 1

The hydrogenation of pseudoionone was carried out in a 243-ml fix-bed reactor with heating/cooling jacket with thermoelements placed in the centre of the reactor and on the reactor wall. Pressure-control valves were provided at the entrance end the exit site of the reactor. The reactor was charged with 162 ml (73 g) of catalyst (0.5% (wt./wt.) Pd on $SiO_2$) and 81 ml of carrier material with 1 part by volume catalyst and 2 parts by volume of carrier in the bottom third of the reactor (entrance site), 2 parts by volume of catalyst and 1 part by volume of carrier in the middle third of the reactor, and catalyst alone at the top third of the reactor (exit site). The reactor was first flushed with nitrogen. The temperature at the entrance site of the reactor was adjusted to 80° C. and substrate, pseudoionone at a rate of 0.6 kg per hour, and hydrogen at a rate of 900 NL (norm liter) per hour were fed from separate storage tanks via a static mixer to the entrance site of the reactor. The hydrogenation was carried out in an up-flow mode. The mass flow was 8.3 kg of feed per hour per kg of catalyst and the pressure was set to 150 bar. The gradient of the maximum temperature in the reactor was 210° C.→170° C. and the temperature at the reactor outlet was adjusted to 80° C. The reaction product was released over a pressure valve into a separator where excess hydrogen was separated from the liquid hydrogenation product, hexahydropseudoionone. The reaction was allowed to proceed for 250 h, with yields of hexahydropseudoionone varying from 94 to 96% over that period (as determined by GC).

EXAMPLE 2

Using the apparatus and procedure described in Example 1 but employing a 0.5% (wt./wt.) Pd on $Al_2O_3$ catalyst (DEGUSSA, E257H/D) pseudoionone was hydrogenated to produce hexahydropseudoionone. The process parameters were as stated below:

| | |
|---|---|
| Pseudoionone (crude) | 0.6 kg/h |
| Hydrogen | 900 NL/h |
| Catalyst amount | 138 g |
| Catalyst volume | 243 ml |
| Pressure | 150 bar |
| Mass flow (WHSV) | 4.3 kg feed/h per kg catalyst |
| Temperature at reactor outlet | 120° C. |
| Gradient of maximum temperature in reactor | 220° C. → 190° C. |

The reaction was allowed to proceed for 3000 h, with yields of hexahydro-pseudoionone varying from 94.6 to 96% over that period (as determined by GC).

EXAMPLE 3

Using the apparatus and procedure described in Example 1 but employing a 0.5% (wt./wt.) Pd on $Al_2O_3$ catalyst (DEGUSSA, E257H/D) 6,10-dimethyl-undeca -4,5,9-triene-2-one (DUTO) was hydrogenated to produce hexahydropseudoionone. The process parameters were as stated below:

| | |
|---|---|
| 6,10-dimethyl-undeca-4,5,9-triene-2-one | 0.6 kg/h |
| Hydrogen | 900 NL/h |
| Catalyst amount | 0.138 kg |
| Catalyst volume | 0.243 l |
| Pressure | 150 bar |
| Mass flow (WHSV) | 4.3 kg feed/h per kg catalyst |
| Temperature at reactor outlet | 120° C. |
| Gradient of maximum temperature in reactor | 220° C. → 190° C. |

The reaction was allowed to proceed for 600 h, with yields of hexahydropseudoionone varying from 92 to 94% over that period (as determined by GC).

EXAMPLE 4

In analogy to the procedure and apparatus described in Example 1 but employing a 0.5% (wt./wt.) Pd on $Al_2O_3$ catalyst (DEGUSSA, E257H/D) 6,10,14-trimethyl -pentadeca-4,5-diene-2-one was hydrogenated to produce 6,10,14-trimethyl-pentadecane-2-one (phytone). The process parameters were as stated below:

| | |
|---|---|
| 6,10,14-trimethyl-pentadeca-4,5-dien-2-on | 0.6 kg/h |
| Hydrogen | 900 NL/h |
| Catalyst amount | 138 g |
| Catalyst volume | 243 ml |
| Pressure | 150 bar |
| Mass flow | 4.3 kg feed/h per kg catalyst |
| Temperature at reactor outlet | 120° C. |
| Gradient of maximum temperature in reactor | 220° C. → 190° C. |

The reaction was allowed to proceed for 350 h, with yields of phytone varying from 92 to 94% over that period (as determined by GC).

EXAMPLE 5

In analogy to the procedure and apparatus described in Example 1 but employing a 0.5% (wt./wt.) Pd on $Al_2O_3$ catalyst (DEGUSSA, E257H/D) geranylacetone was hydrogenated to produce hexahydropseudoionone. The process parameters were as stated below:

| | |
|---|---|
| Geranylacetone | 0.6 kg/h |
| Hydrogen | 900 NL/h |
| Catalyst amount | 138 g |
| Catalyst volume | 243 ml |
| Pressure | 150 bar |
| Mass flow | 4.4 kg feed/h per kg catalyst |
| Temperature at reactor outlet | 120° C. |
| Gradient of maximum temperature in reactor | 188° C. → 152° C. |

The reaction was allowed to proceed for 21 days, with yields of hexahydropseudoionone varying from 85 to 97% over that period (as determined by GC). The conversion of geranylacetone was 100%. There was no formation of partially hydrogenated intermediates.

EXAMPLE 6

The process of Example 5 was repeated using pressures of 50 and 100 bar. Lowering the pressure had no effect on conversion and yield.

EXAMPLE 7

The process of Example 6 was repeated using 450 NL/h $H_2$, i.e. half the hydrogen feed. No effect on conversion and yield was observed.

What is claimed is:

1. Process for the preparation of saturated aliphatic ketones which comprises hydrogenating an allenically unsaturated ketone in a continuous fixed-bed mode in the absence of a solvent in the presence of a catalyst comprising a noble metal deposited on a carrier selected from $ZrO_2$, $TiO_2$, $SiO_2$ and $Al_2O_3$ wherein the amount of noble metal is 0.1 to 5% (wt./wt.).

2. A process as in claim 1 wherein the noble metal is palladium.

3. A process as in claim 1 wherein the amount of the noble metal deposited on the carrier is 0.2 to 0.7% (wt./wt.).

4. A process as in claim 1 wherein the catalyst is distributed within inert carrier material.

5. A process as in claim 4 wherein the ratio of catalyst to inert carrier material is about 1:1 parts by volume.

6. A process as in claim 1 wherein the allenically unsaturated ketone is 6,10-dimethyl-undeca-4,5,9-trien-2-one, or 6,10,14-trimethyl-pentadeca-4)5-dien-2-one.

7. A process as in claim 1 wherein the hydrogenation is carried out at about 50 to about 200 bar and about 70° C. to about 250° C.

8. A process as in claim 1 wherein the throughput is 1-20 kg of feed per kg of catalyst per hour.

9. A process as in claim 1 wherein the mass flow is 3-15 kg of feed per kg of catalyst per hour.

10. A process as in claim 1 wherein the catalyst is distributed within unloaded carrier material to provide in the reactor an increase of the concentration of noble metal from the entrance to the exit of the flow of the reactants.

* * * * *